United States Patent [19]

Glamkowski et al.

[11] Patent Number: 4,751,223

[45] Date of Patent: Jun. 14, 1988

[54] ANTIINFLAMMATORY AND ANALGESIC AMINOALKYL TETRACYCLIC BENZODIAZEPINES

[75] Inventors: Edward J. Glamkowski, Warren; Yulin Chiang, Convent Station, both of N.J.; Frederick J. Ehrgott, Jr., Norwich, Conn.

[73] Assignee: Hoechst-Roussel Pharmaceuticals, Inc., Somerville, N.J.

[21] Appl. No.: 918,748

[22] Filed: Oct. 14, 1986

[51] Int. Cl.[4] .................... A61K 31/55; C07D 487/06
[52] U.S. Cl. ...................................... 514/219; 540/556
[58] Field of Search ......................... 540/556; 514/219

[56] References Cited

U.S. PATENT DOCUMENTS

| 4,186,199 | 1/1980 | Glamkowski et al. | 540/556 |
|---|---|---|---|
| 4,192,874 | 3/1980 | Glamkowski et al. | 540/556 |
| 4,405,631 | 9/1983 | Kosley, Jr. et al. | 546/208 X |
| 4,438,120 | 3/1984 | Rajagopalan | 514/219 |
| 4,447,361 | 5/1984 | Taylor, Jr. | 540/307 X |
| 4,521,537 | 1/1985 | Kosley, Jr. et al. | 514/302 |

FOREIGN PATENT DOCUMENTS 129692  1/1985  European Pat. Off. .

OTHER PUBLICATIONS

Blickenstaff, et al., Chem. Abstracts, vol. 82 (1975), entry 4219u.
Glamkowski, et al., J. Heterocyclic Chem., 16, 865 (1979).
Glamkowski, et al., J. Med. Chem., 23, 1380 (1980).

Primary Examiner—Donald G. Daus
Assistant Examiner—William A. Teoli, Jr.
Attorney, Agent, or Firm—Tatsuya Ikeda

[57] ABSTRACT

There are disclosed compounds of the formula

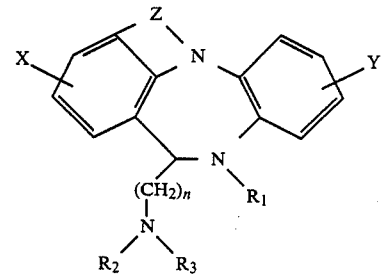

where X and Y are independently hydrogen, loweralkyl, trifluoromethyl or halogen; Z is —$CH_2CH_2$—, —CH=CH— or —$CH_2CH_2CH_2$—; n is 1, 2 or 3; $R_1$ is hydrogen, loweralkanoyl, aroyl, ethoxycarbonyl, phenoxycarbonyl, loweralkylaminocarbonyl, arylaminocarbonyl, loweralkyl or arylmethyl; $R_2$ is hydrogen or loweralkyl; $R_3$ is hydrogen, loweralkyl, ethoxycarbonyl, loweralkanoyl or arylloweralkyl, or $R_2$ and $R_3$ taken together is isopropylidene; with the proviso that when n is 3, X, Y and $R_1$ are all hydrogen and Z is —$CH_2CH_2$—, $R_2$ and $R_3$ can not both be methyl. These compounds display antiinflammatory and analgesic activities.

57 Claims, No Drawings

4,751,223

ANTIINFLAMMATORY AND ANALGESIC AMINOALKYL TETRACYCLIC BENZODIAZEPINES

The present invention relates to compounds of the formula

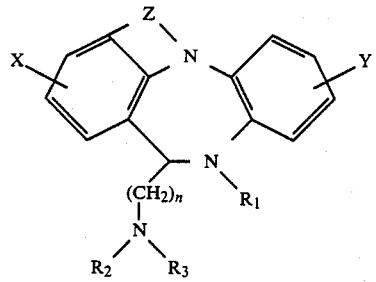

(I)

where X and Y are independently hydrogen, loweralkyl, trifluoromethyl or halogen; Z is —CH$_2$CH$_2$—, —CH=CH— or —CH$_2$CH$_2$CH$_2$—; n is 1, 2 or 3; R$_1$ is hydrogen, loweralkanoyl, aroyl, ethoxycarbonyl, phenoxycarbonyl, loweralkylaminocarbonyl, arylaminocarbonyl, loweralkyl or arylmethyl; R$_2$ is hydrogen or loweralkyl; R$_3$ is hydrogen, loweralkyl, ethoxycarbonyl, loweralkanoyl or arylloweralkyl, or R$_2$ and R$_3$ taken together is isopropylidene; with the proviso that when n is 3, X, Y and R$_1$ are all hydrogen and Z is —CH$_2$CH$_2$—, R$_2$ and R$_3$ can not both be methyl; which display antiinflammatory and analgesic activities, pharmaceutical compositions comprising these compounds and a method of alleviating inflammation and/or pain by use of these compounds.

Unless otherwise stated or indicated, the following definitions shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1 or 2 substituents each of which being independently loweralkyl, loweralkoxy, halogen or CF$_3$.

The term loweralkanoyl shall mean a group obtained by removing a hydroxy group from the carboxyl group of a loweralkanoic acid, and thus it includes for instance formyl, acetyl and the like.

The term aroyl shall mean arylcarbonyl, the term aryl having the meaning as defined above.

It should be noted that an asymmetric center exists at the ring carbon carrying the —(CH$_2$)$_n$NR$_2$R$_3$ group in Formula I. Throughout the specification and appended claims, a given chemical structure, formula or name shall encompass all optical isomers including racemic mixture.

The compounds of this invention are prepared by following one or more of the steps described below. Throughout the description of the synthetic steps, the definitions of X, Y, Z, n, R$_1$, R$_2$ and R$_3$ are as given above unless otherwise stated or indicated, and other nomenclatures used below shall have the definitions given at their respective first appearances unless otherwise stated or indicated.

STEP A

A compound of formula II where Z' is —CH$_2$CH$_2$— or —CH$_2$CH$_2$CH$_2$— is cyclized in the presence of POCl$_3$ to afford a compound of formula III.

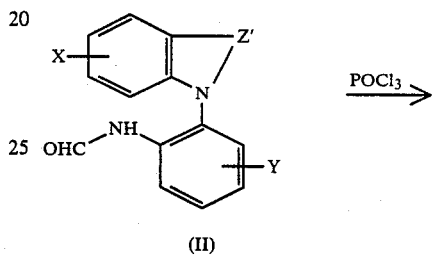

(II)

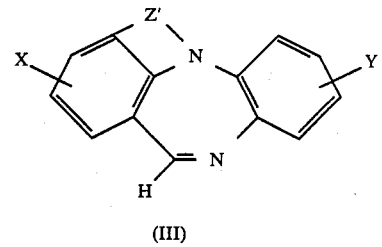

(III)

Said cyclization is conducted typically by refluxing compound II in phosphorus oxychloride for a few hours.

A reaction scheme for preparing the starting compound II where Z is —CH$_2$CH$_2$— is described, for instance, in E. Glamkowski and M. Fortunato, J. Heterocyclic Chem., 16, 865-869 (1979). Substantially the same reaction scheme can be used for preparing the compound II where Z' is —CH$_2$CH$_2$CH$_2$—.

STEP B

A compound of formula IV is dehydrogenated to afford a compound of formula V.

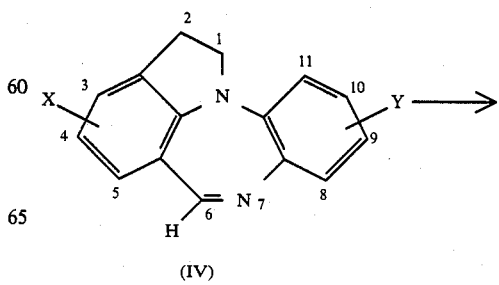

(IV)

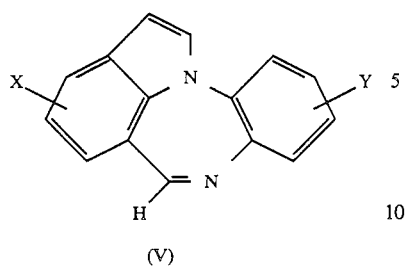

(V)

Said dehydrogenation is conducted typically in the presence of 2,3-dichloro-5,6-dicyano-1,4-benzoquinone and a suitable solvent such as toluene and refluxing the reaction mixture under an inert atmosphere for a few hours.

STEP C

A compound of formula VI prepared in STEP A or B is reacted with a Grignard reagent of formula VII where $R_4$ is loweralkyl and $R_5$ is loweralkyl or aryllower-alkyl to afford a compound of formula VIII.

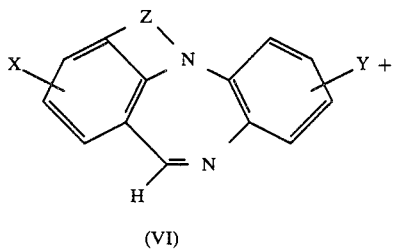

(VI)

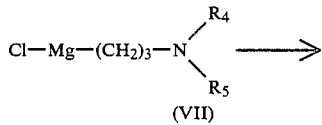

(VII)

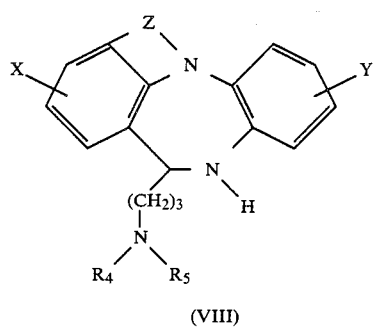

(VIII)

The Grignard reagent VII is prepared from magnesium and the compound $Cl-(CH_2)_3-NR_4R_5$ typically in a suitable medium such as anhydrous tetrahydrofuran and in the presence of 1-bromo-2-chloroethane or 1,2-dibromoethane which facilitates the initiation of the Grignard reaction. Usually, the reaction mixture is heated at reflux under an inert gas atmosphere for about an hour and thereafter cooled to below room temperature. The reaction between compound VI and the Grignard reagent VII is conducted typically by adding the above mixture to a stirred ice cold mixture consisting of compound VI and anhydrous tetrahydofuran and further stirring the resultant mixture for a short period of time such as less than one hour.

STEP D

Compound VIII is reacted with a compound of the formula $R_6COCl$ where $R_6$ is loweralkyl or aryl to afford a compound of formula IX below.

VIII + $R_6COCl \longrightarrow$

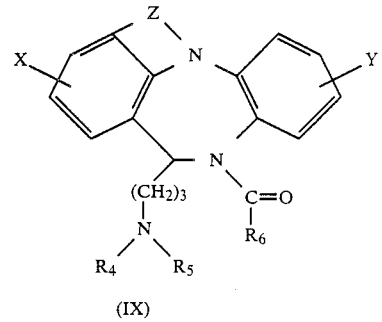

(IX)

The above reaction is conducted typically in the presence of an acid scavenger such as sodium bicarbonate or collidine in a suitable medium such as anhydrous chloroform and stirring the reaction mixture at room temperature for a few hours or less.

STEP E

Compound VIII is reacted with formic-acetic mixed anhydride to afford a compound of formula X.

VIII + $HCOOCOCH_3 \longrightarrow$

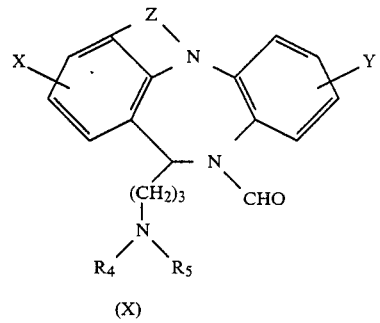

(X)

The above reaction is conducted typically by first preparing formic-acetic mixed anhydride from acetic anhydride and formic acid and then adding the mixed anhydride to a solution of compound VIII in a suitable solvent such as chloroform and stirring the resultant mixture at room temperature for a short period of time such as one hour or less.

STEP F

Compound VIII is reacted with a chloroformate of the formula $ClCO_2R_7$ where $R_7$ is ethyl or phenyl to afford a compound of formula XI.

VIII + $ClCO_2R_7 \longrightarrow$

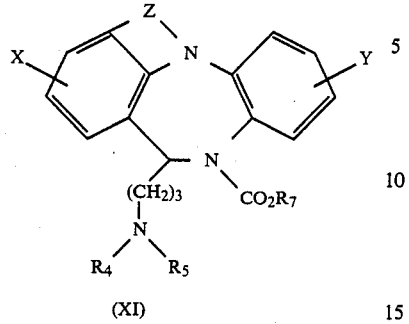

(XI)

The above reaction is typically conducted in a suitable medium such as chloroform and refluxing the reaction mixture overnight.

STEP G

Compound VIII is reacted with an isocyanate compound of the formula R$_8$NCO where R$_8$ is loweralkyl or aryl to afford a compound of formula XII below.

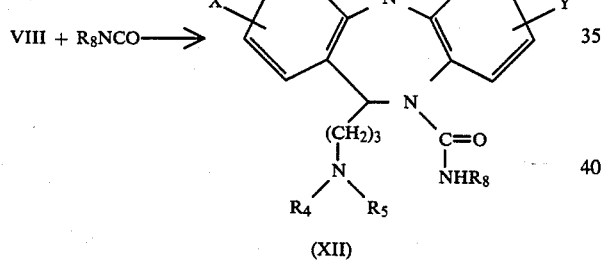

(XII)

STEP H

A compound of formula XIII where R$_9$ is hydrdgen, loweralkyl or aryl prepared in STEP D or E is reduced with borane to afford a compound of formula XIV.

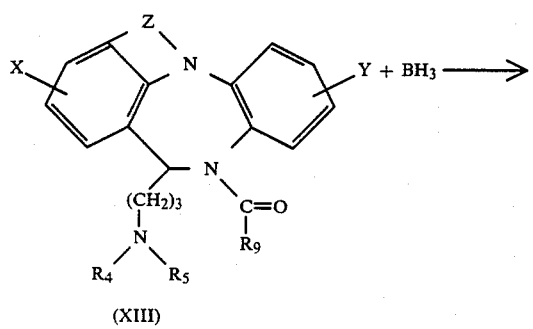

(XIII)

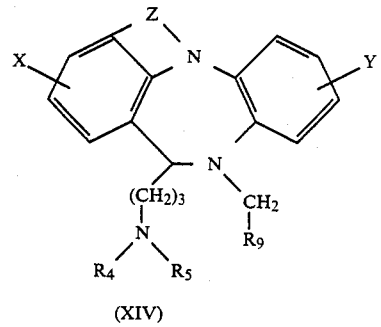

(XIV)

The above reduction is conducted typically by adding a solution of borane-dimethylsulfide complex in a suitable solvent such as tetrahydrofuran to a solution of compound XIII in the same solvent, stirring the mixture at room temperature for a few hours and then at reflux for less than one hour.

STEP I

A compound of formula XV prepared in one of STEPS C through H is reacted with ethyl chloroformate to afford a compound of formula XVI.

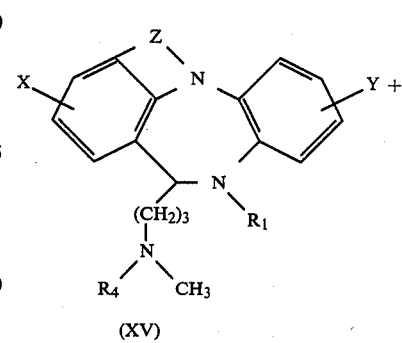

(XV)

ClCO$_2$C$_2$H$_5$ ⟶

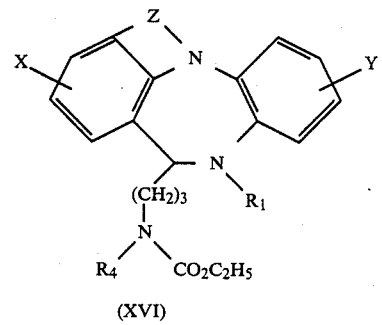

(XVI)

The above reaction is conducted typically in the presence of an acid scavenger in a suitable medium such as benzene and refluxing the reaction mixture for about a day.

STEP J

Compound XVI is hydrolyzed to afford a compound of formula XVII.

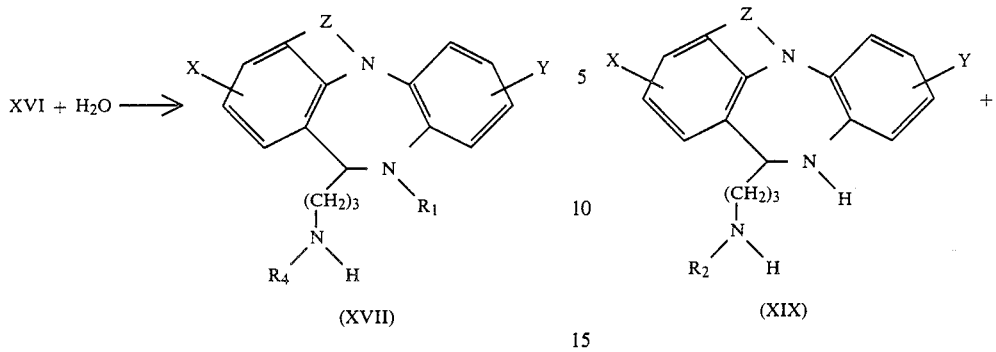

(XVII)

The above hydrolysis is conducted typically by preparing a mixture of compound XVI, ethanol and aqueous alkali solution and refluxing the mixture for a few days.

STEP K

For preparing a compound of formula XVIII, compound VI is reacted with the Grignard reagent Cl—Mg—(CH$_2$)$_3$—N(CH$_2$C$_6$H$_5$) in substantially the same manner as in STEP C and the product is subjected to hydrogenolysis in the presence of a suitable catalyst such as Pd/C in a routine manner known to the art.

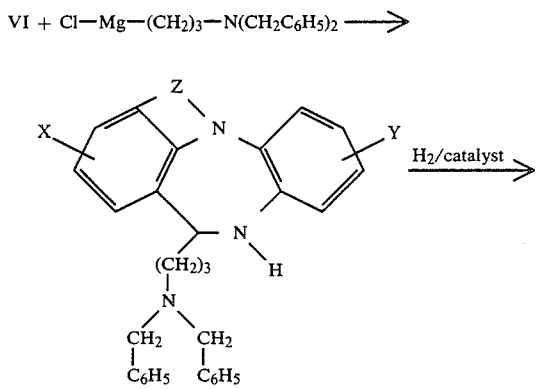

(XVIII)

STEP L

A compound of formula XIX obtained from STEP J or K is reacted with R$_{10}$C(O)OMe or R$_{10}$C(O)OEt where R$_{10}$ is hydrogen or loweralkyl to afford a compound of formula XX.

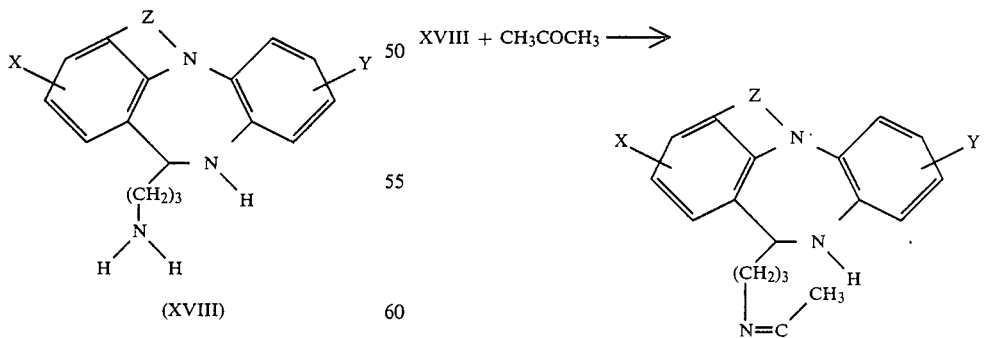

(XX)

Where R$_{10}$ is hydrogen, the above reaction is typically conducted by preparing a mixture of compound XIX, methyl formate and ethanol and refluxing the mixture overnight. Where R$_{10}$ is loweralkyl, the above reaction is conducted by making a suitable selection of reaction conditions. Thus, for instance, where R$_{10}$ is methyl, compound XIX is reacted with ethyl acetate in anhydrous tetrahydrofuran at room temperature overnight.

STEP M

Compound XVIII is reacted with acetone to afford a compound of formula XXI (Schiff base).

XVIII + CH$_3$COCH$_3$ ⟶

(XXI)

The above reaction is conducted typically by simply mixing compound XVIII with acetone and maintaining the mixture at room temperature for several hours.

STEP N

Compound XXI is reduced with sodium cyanoborohydride to afford a compound of formula XXII.

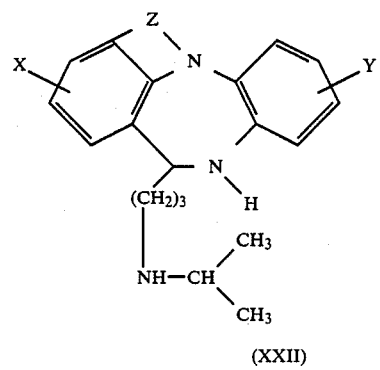

The above reduction is typically conducted in a suitable medium such as acetonitrile and stirring the reaction mixture at 0°–20° for a few hours.

STEP O

Compound VI is reacted with sodium cyanide to afford a compound of formula XXIII.

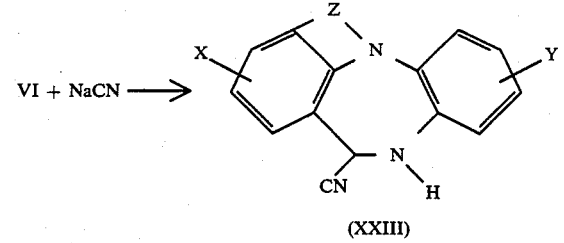

The above reaction is conducted typically by stirring a mixture of compound VI, sodium cyanide and acetic acid in a suitable medium such as ethyl acetate at room temperature for about a day.

STEP P

Compound VI is reacted with acetonitrile in the presence of a strong base such as n-butyllithium to afford a compound of formula XXIV.

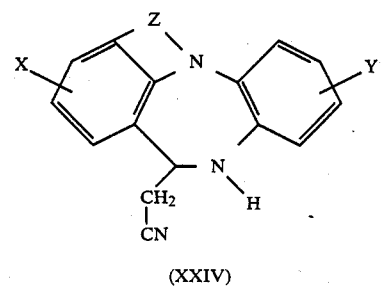

The above reaction is conducted typically by first reacting n-butyllithium with acetonitrile in a suitable solvent such as tetrahydrofuran at a low temperature such as about −60° C. for less than one hour to obtain the anion of acetonitrile and thereafter adding to the reaction mixture a solution of compound VI in the same solvent, removing the cold bath and stirring the resultant mixture for a few hours.

STEP Q

A compound of formula XXV where m is 0 or 1 prepared in STEP O or P is reduced with lithium aluminum hydride or diisobutylaluminum hydride to afford a compound of formula XXVI.

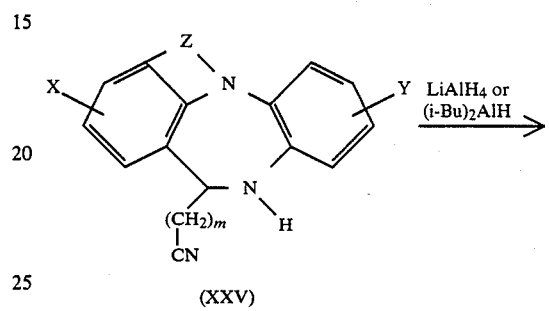

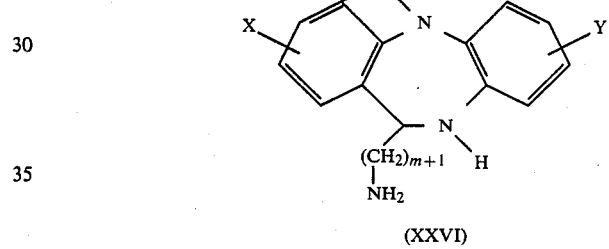

The above reduction is conducted typically in a suitable medium such as anhydrous tetrahydrofuran or dichloromethane and stirring the reaction mixture at room temperature for a few hours.

STEP R

Compound XXVI is reacted with $R_{11}C(O)OMe$ or $R_{11}C(O)OEt$ where $R_{11}$ is hydrogen, loweralkyl or arylloweralkyl in substantially the same manner as in STEP L to afford a compound of formula XXVII.

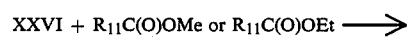

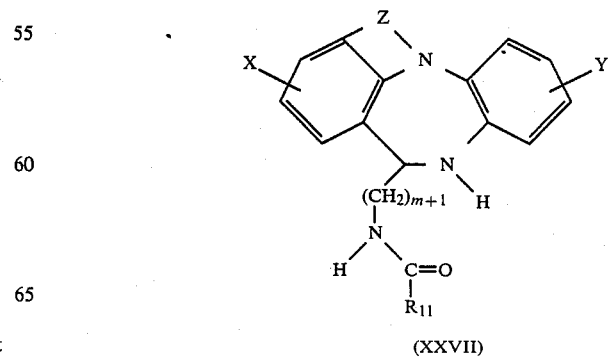

STEP S

Compound XXVII is reduced with lithium aluminum hydride to afford a compound of formula XXVIII.

XXVII + LiAlH₄ ⟶

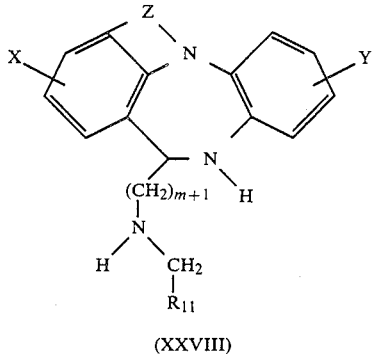

(XXVIII)

The above reaction is conducted typically in a suitable medium such as anhydrous tetrahydrofuran and stirring the reaction mixture at room temperature overnight.

STEP T

The side-chain amino hydrogen of compound XXVIII can be converted to loweralkyl by conducting acylation in substantially the same manner as in STEP L and reducing the product with LiAlH₄ in substantially the same manner as in STEP S.

Thus by virtue of STEPS Q through T, compounds of formula XXIX where $R_{12}$ is hydrogen, loweralkyl, loweralkanoyl or arylloweralkyl are obtained. The remaining compounds, namely, compounds of formula I where n is 1 or 2; and $R_1$ is other than hydrogen, and/or $R_3$ is ethoxycarbonyl, and/or $R_2$ and $R_3$ taken together is isopropylidene can be prepared by utilizing the various reaction steps described earlier for making compounds of formula I where n is 3, namely, STEPS D, E, F, G, H, I, M and N.

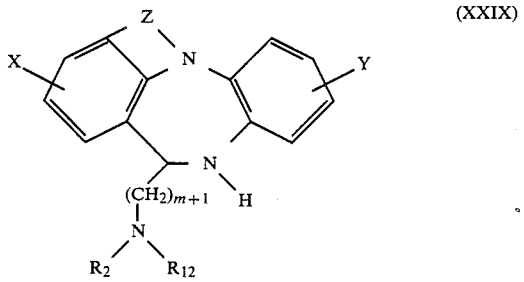

(XXIX)

The compounds of the present invention are useful as antiinflammatory agents due to their ability to suppress inflammation in mammals. The activity of the compounds is demonstrated in the carrageenin induced rat paw edema antinflammatory assay [Proc. Soc. Exptl. Biol. Med., III 544 (1962), and J. Pharmacol. Exp., 141 (1963)]. The results of the antinflammatory test of some of the compounds of this invention are given in Table I along with the result of a standard compound.

TABLE 1

| Inhibition of Carrageenan-Induced Rat Paw Edema | |
|---|---|
| Compound | Percent Inhibition |
| 7-acetyl-N,N—dimethyl-1,2,6,7-tetrahydrobenzo[b]pyrrolo[3,2,1-jk][1,4]benzodiazepine-6-propanamine hydrochloride | 42% at 100 mg/kg, p.o. |
| N,N—dimethyl-7-(methylamino)-carbonyl-1,2,6,7-tetrahydro-benzo[b]pyrrolo[3,2,1-jk][1,4]-benzodiazepine-6-propanamine hydrochloride | 42% at 100 mg/kg, p.o. |
| 4-bromo-N,N—dimethyl-6,7-dihydrobenzo[b]pyrrolo-[3,2,1-jk][1,4]benzodiazepine-6-propanamine fumarate hemihydrate | 34% at 100 mg/kg, p.o. |
| N—(isopropyl)-1,2,6,7-tetrahydrobenzo[b]pyrrolo-[3,2,1-jk][1,4]benzodiazepine-6-methanamine dihydrochloride hemihydrate (prior art compound) | 35% at 100 mg/kg, p.o. |
| Phenylbutazone | ED₅₀ = 50 mg/kg, p.o. |

The antiinflammatory activities of the compounds of the present invention are also demonstrated in the adjuvant-induced polyarthritis syndrome in rats. This activity was measured by a procedure similar to that described by C. M. Pearson and F. D. Wood, Arthritis and Rheumatism, 2, 440 (1959).

Groups of 10 male Charles River-Wistar Lewis rats weighing 150 to 175 g were individually housed and maintained on a regular rat chow diet. Water was given ad libitum. The adjuvant was prepared by suspending 75 mg of *Mycobacterium butyricum* (Difco Laboratories, Detroit, Michigan) in 10 ml of white paraffin oil with continuous stirring for 2 hours at room temperature prior to administration. Test compounds are prepared by suspending the drug in water, adding one drop of Tween 80 per 10 ml of suspension, and homogenizing. The adjuvant suspension (0.1 ml) was injected into the footpad of the left hind paw of the rat. Test compound suspensions were administered orally (10 ml/kg) the day before adjuvant suspension injection and the administration of drug was continued for 21 days. One group of ten rats was used for the test drug. Standard, adjuvant-injected control and non-injected control groups are run along with the test drug. Control animals received vehicle (10 ml/kg). Three doses of test drug and one dose of standard preparation were used. Injected and non-injected paw volumes were determined on the day the adjuvant suspension was given, and on subsequent days thereafter (usually days 5, 10, 18, and 21) by the method of C. A. Winter, et al., Proc. Soc. Exp. Biol. Med., 111, 544 (1962).

The percent inhibition of paw volume (injected and non-injected hind paw) was calculated by the following formula:

% Inhibition =

$$\frac{\text{Mean Paw Volume Change of Injected (or Non-injected) Control} - \text{Mean Paw Volume Change of Drug Treated}}{\text{Mean paw Volume Change of Injected (or Non-Injected) Control}} \times 100$$

ED₅₀-values, i.e., the dose at which the drug affects a 50% inhibition of paw volume, were estimated by the method of J. T. Litchfield and F. Wilcoxon, J. Pharm.

Exp. Ther., 96, 99 (1949) and statistically evaluated by means of the student "t" test. The test results of some of the compounds of the present invention are presented in Table 2 along with the results of a standard compound. Also included in Table 2 is the result of N,N-dimethyl-1,2,6,7-tetrahydrobenzo[b]pyrrolo[3,2,1-jk[1,4]-benzodiazepine-6-propanamine (corresponding to n=3, X=Y=H, $R_2$=$R_3$=$CH_3$ and Z=—$CH_2CH_2$— in Formula I), which was previously disclosed in an article as an inactive analog of an active antidepressant (E. J. Glamkowski et al., J. Med. Chem., 23, 1380 (1980)), but which has now been found in this invention to be active as an antiinflammatory agent.

TABLE 2

| Adjuvant-Induced Polyarthritis In Rats | | |
|---|---|---|
| Compound | Adjuvant-treated paw | Non-Injected paw |
| 4-bromo-N,N—dimethyl-1,2,6,7-tetrahydrobenzo[b]-pyrrolo[3,2,1-jk][1,4]-benzodiazepine-6-propanamine dihydrochloride | $ED_{50}$ = 106 mg/kg, p.o. | $ED_{50}$ = 42.6 mg/kg, p.o. |
| 1,2,6,7-tetrahydrobenzo-[b]pyrrolo[3,2,1-jk][1,4]-benzodiazepine-6-methanamine | 14% at 25 mg/kg, p.o. | 91% at 25 mg/kg, p.o. |
| N,N—Dimethyl-1,2,6,7-tetrahydrobenzo[b]pyrrolo-[3,2,1-jk][1,4]benzodiazepine-6-propanamine dihydrochloride (prior art compound) | $ED_{50}$ = 86.6 mg/kg, p.o. | $ED_{50}$ = 24.3 mg/kg, p.o. |
| Phenylbutazone | $ED_{50}$ = 14 mg/kg, p.o. | $ED_{50}$ = 9.4 mg/kg, p.o. |

The compounds of the present invention are also useful as analgesic agents due to their ability to alleviate pain in mammals. The activity of the compounds is demonstrated in the 2-phenyl-1,4-benzoquinone induced writhing test in mice, a standard assay for analgesia [Proc. Soc. Exptl. Biol. Med., 95, 729 (1957)]. Table 3 shows the test results of some of the compounds of this invention along with the result of a standard compound. Also included in Table 3 is the aforementioned compound N,N-dimethyl-1,2,6,7-tetrahydrobenzo[b-]pyrrolo[3,2,1-jk][1,4]benzodiazepine-6-propanamine which has now been found in this invention to be active as an analgesic agent.

TABLE 3

| Phenylquinone Induced Writhing in Mice | |
|---|---|
| Compound | Percent Inhibition |
| N,N—dimethyl-7-ethoxycarbonyl-1,2,6,7-tetrahydrobenzo[b]-pyrrolo[3,2,1-jk][1,4]-benzodiazepine-6-propanamine hydrochloride | 41% at 20 mg/kg, s.c. |
| 9-bromo-N,N—dimethyl-1,2,6,7-tetrahydrobenzo[b]pyrrolo-[3,2,1-jk][1,4]benzodiazepine-6-propanamine dihydrochloride | 60% at 20 mg/kg, s.c. |
| N—(isopropyl)-1,2,6,7-tetrahydrobenzo[b]pyrrolo-[3,2,1-jk][1,4]benzodiazepine-6-methanamine dihydrochloride hemihydrate | 48% at 20 mg/kg, s.c. |
| N,N—Dimethyl-1,2,6,7-tetrahydrobenzo[b]pyrrolo-[3,2,1-jk][1,4]benzodiazepine-6-propanamine dihydrochloride (prior art compound) | $ED_{50}$ = 13.4 mg/kg, s.c. |
| Propoxyphene | $ED_{50}$ = 3.9 mg/kg, s.c. |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purposes of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amount used.

For the purposes of parenteral therapeutic administration, the active compounds of the invention may be incorporated into a solution or suspension. These preparations should contain at least 0.1% of active compounds, but may be varied depending upon the particular form and may conveniently be between 4% and about 70% of the weight of the unit. The amount of active compound in such compositions is such that a suitable dosage will be obtained. Preferred compositions and preparations according to the present invention are prepared so that a parenteral dosage unit contains between 0.5 to 100 milligrams of active compounds.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

7-benzoyl-N,N-dimethyl-1,2,6,7-tetrahydrobenzo[b]pyrrolo[3,2,1-jk][1,4]benzodiazepine-6-propanamine;
7-acetyl-N,N-dimethyl-1,2,6,7-tetrahydrobenzo[b]pyrrolo[3,2,1-jk][1,4]benzodiazepine-6-propanamine;
N,N-dimethyl-7-ethoxycarbonyl-1,2,6,7-tetrahydrobenzo[b]pyrrolo[3,2,1-jk][1,4]benzodiazepine-6-propanamine;
N,N-dimethyl-7-(methylamino)carbonyl-1,2,6,7-tetrahydrobenzo[b]pyrrolo[3,2,1-jk][1,4]benzodiazepine-6-propanamine;
N,N-dimethyl-7-(phenylamino)carbonyl-1,2,6,7-tetrahydrobenzo[b]pyrrolo[3,2,1-jk][1,4]benzodiazepine-6-propanamine;
4-bromo-N,N-dimethyl-1,2,6,7-tetrahydrobenzo[b]pyrrolo[3,2,1-jk][1,4]benzodiazepine-6-propanamine;
4-bromo-7-methyl-N,N-dimethyl-1,2,6,7-tetrahydrobenzo[b]pyrrolo[3,2,1-jk][1,4]benzodiazepine-6-propanamine;
N-[3-[7-acetyl-1,2,6,7-tetrahydrobenzo[b]pyrrolo[3,2,1-jk][1,4]benzodiazepine-6-yl]propyl]-N-methylcarbamic acid ethyl ester;
7-acetyl-N-methyl-1,2,6,7-tetrahydrobenzo[b]pyrrolo[3,2,1-jk]1,4]benzodiazepine-6-propanamine;
N-methyl-N-phenylmethyl-1,2,6,7-tetrahydrobenzo[b]pyrrolo3,2,1-jk][1,4]benzodiazepine-6-propanamine;
4-bromo-N,N-dimethyl-6,7-dihydrobenzo[b]pyrrolo[3,2,1-jk][1,4]benzodiazepine-6-propanamine;
9-bromo-N,N-dimethyl-1,2,6,7-tetrahydrobenzo[b]pyrrolo[3,2,1-jk][1,4]benzodiazepine-6-propanamine;
N,N-dimethyl-9-trifluoromethyl-1,2,6,7-tetrahydrobenzo[b]pyrrolo[3,2,1-jk][1,4]benzodiazepine-6-propanamine;
4-bromo-N,N-dimethyl-7-formyl-1,2,6,7-tetrahydrobenzo[b]pyrrolo[3,2,1-jk][1,4]benzodiazepine-6-propanamine;
1,2,6,7-tetrahydrobenzo[b]pyrrolo[3,2,1-jk][1,4]benzodiazepine6-methanamine;
N-(methylethylidene)-1,2,6,7-tetrahydrobenzo[b]pyrrolo[3,2,1-jk][1,4]benzodiazepine-6-methanamine;
N-(isopropyl)-1,2,6,7-tetrahydrobenzo[b]pyrrolo[3,2,1-jk][1,4]benzodiazepine-6-methanamine dihydrochloride;
N-[[7-formyl-1,2,6,7-tetrahydrobenzo[b]pyrrolo[3,2,1-jk][1,4]benzodiazepine-6-yl]methyl]-formamide;
N-methyl-7-methyl-1,2,6,7-tetrahydrobenzo[b]pyrrolo[3,2,1-jk][1,4]benzodiazepine-6-methanamine;
N-[[1,2,6,7-tetrahydrobenzo[b]pyrrolo[3,2,1-jk][1,4]benzodiazepine-6-yl]methyl]-formamide;
N-methyl-1,2,6,7-tetrahydrobenzo[b]pyrrolo[3,2,1-jk][1,4]benzodiazepine-6-methanamine;
1,2,6,7-tetrahydrobenzo[b]pyrrolo[3,2,1-jk][1,4]benzodiazepine6-ethanamine; and
N-[[1,2,6,7-tetrahydrobenzo[b]pyrrolo[3,2,1-jk][1,4]benzodiazepine-6-yl]ethyl]-acetamide, including the racemates and the + and − optical isomers of the above compounds.

The following examples are given for the purpose of illustrating this invention:

EXAMPLE 1

N,N-Dimethyl-1,2,6,7-tetrahydrobenzo[b]pyrrolo[3,2,1-jk][1,4]benzodiazepine-6-propanamine dihydrochloride A Grignard reagent was prepared under nitrogen in a flame dried 100 ml three-necked round bottom flask as follows: A 2 ml portion of a solution prepared from 7.14 g of 3-(dimethylamino)propyl chloride, 1.61 ml of 1-bromo-2-chloroethane and 28.7 ml of freshly distilled tetrahydrofuran (THF) was added to a stirred slurry of 1.94 g of magnesium shavings in 5 ml of dry tetrahydrofuran. The mixture became cloudy within 1 minute and a vigorous reaction ensued. The remaining solution was added dropwise over 75 minutes and the reaction was controlled with periodic cooling using an ice-water bath. Twenty minutes after the end of the addition, the reaction mixture was heated at reflux for 40 minutes and then cooled to 10°–15° C.

The freshly prepared Grignard reagent was added dropwise with a syringe to a rapidly stirred, ice cold slurry of 5.0 g of 1,2-dihydrobenzo[b]pyrrolo[3,2,1-jk][1,4]benzodiazepine in 76 ml of dry tetrahydrofuran under nitrogen. A purple-to-red-to-brown color change occurred over the course of the addition. Thin layer chromatographic (TLC) analysis (silica gel/ethyl acetate) conducted 25 minutes after the end of the addition showed no starting material.

The product was poured onto a mixture of 200 ml of ice and 25 ml of concentrated hydrochloric acid and the mixture was made basic with concentrated ammonium hydroxide. The free base was extracted into trichloromethane (400 ml total) and washed with water (400 ml) and brine (400 ml), dried over anhydrous sodium sulfate, and concentrated to afford 5.86 g of an oil. Conversion to the hydrochloric acid salt (isopropanol/ether/ethereal hydrogen chloride) gave 6.58 g of a solid. Recrystallization from hot methanol-ether afforded 5.43 g of pure dihydrochloride salt, m.p. 228°–230°.

ANALYSIS:
Calculated for $C_{20}H_{25}N_3 \cdot 2HCl$: 63.16% C; 7.15% H; 11.05% N;
Found: 63.36% C; 6.91% H; 11.04% N.

EXAMPLE 2

7-Benzoyl-N,N-dimethyl-1,2,6,7-tetrahydrobenzo[b]pyrrolo[3,2,1jk][1,4]benzodiazepine-6-propanamine hydrochloride To a suspension consisting of 1.26 g of powdered sodium bicarbonate, 100 ml of chloroform and 3.38 g of N,N-dimethyl1,2,6,7-tetrahydrobenzo[b]pyrrolo[3,2,1-jk][1,4]benzodiazepine6-propanamine was added, all at once under nitrogen, 1.5 ml of benzoyl chloride. A slight rise in temperature occurred. After 3.5 hours at ambient temperature TLC showed no starting material. This mixture was diluted with 100 ml of water, and after a few minutes of stirring, it was poured into a separatory funnel, and the phases were separated. The chloroform phase was washed with saturated sodium chloride solution (50 ml), dried over anhydrous sodium sulfate, filtered and concentrated in vacuo to a foam, which was triturated to a solid with petroleum ether. The solid was filtered, washed and dried to afford 4.52 g of a solid. This material was dissolved in 25 ml of methanol. Addition of 10 ml of hydrogen chloride-saturated ether solution produced a solution acidic to pH paper. Addition of seeds prepared in a test tube led to an immediate crystallization. After stirring for several hours at room temperature, the solid was filtered, washed with 1 ether/methanol solution, and dried to afford 3.23 g of solid. Recrystallization from boiling isopropanol afforded 2.55 g of microfine crystals, m.p. 250°-252° C.

ANALYSIS:
Calculated for $C_{27}H_{29}N_3O.HCl$: 72.38% C; 6.75% H; 9.38% N;
Found: 72.37% C; 6.61% H; 9.31% N.

EXAMPLE 3

7-Acetyl-N,N-dimethyl-1,2,6,7-tetrahydrobenzo[b]pyrrolo[3,2,1-jk][1,4]benzodiazepine-6-propanamine hydrochloride To a stirred mixture of 5.26 g of N,N-dimethyl-1,2,6,7tetrahydrobenzo[b]pyrrolo[3,2,1-jk][1,4]benzodiazepine-6-propanamine, 2.15 g of powdered sodium bicarbonate and 100 ml of dry chloroform was added, under nitrogen, 1.5 ml of acetyl chloride. After 30 minutes at ambient temperature, TLC showed complete reaction. The mixture was treated with 100 ml of distilled water and stirred vigorously for a few minutes. The phases were separated and the chloroform phase was washed with 50 ml of saturated sodium chloride solution. After drying over anhydrous sodium sulfate, filtration and concentration in vacuo afforded a gum weighing 6.38 g. Trituration with ether caused solidification to occur. The mixture was reconcentrated in vacuo to a solid. This material was triturated with petroleum ether, filtered, and dried to afford 5.27 g of solid. The crude solid was dissolved in a mixture of 10 ml of methanol and 20 ml of ether. Addition of 4 ml of hydrogen chloride-saturated ether caused rapid precipitation of the hydrochloride salt. An additional 25 ml of ether was added to make the mixture more fluid The crude salt was filtered off, washed with a 4:1 ether/methanol mixture and dried to afford 4.65 g of a solid. This material was recrystallized by dissolving it in 75 ml of absolute ethanol and adding 150 ml of ether with tirring. The solid was filtered, washed with ether and dried to afford 4.15 g of product, m.p. 221°-223° C.

ANALYSIS: Calculated for $C_{22}H_{27}N_3O.HCl$: 68.46%C; 7.31%H; 10.89%N; Found: 68.18%C; 7.25%H; 10.68%N;

EXAMPLE 4

N,N-Dimethyl-7-ethoxycarbonyl-1,2,6,7-tetrahydrobenzo[b]pyrrolo[3,2,1-jk][1,4]benzodiazepine-6-propanamine hydrochloride A stirred solution of 6.1 g of N,N-dimethyl-1,2,6,7-tetrahydrobenzo[b]pyrrolo[3,2,1-jk][1,4]benzodiazepine-6-propanamine in 100 ml of chloroform was treated at room temperature with 2.1 ml of ethyl chloroformate. A thick solid precipitated out of solution within 5 minutes. After stirring the mixture for 4.5 hours at room temperature under nitrogen, another 50 ml of chloroform was added and the mixture was refluxed overnight. TLC at this point showed the reaction to be about half complete, with some solid still undissolved. Dilution with 500 ml of chloroform and overnight reflux produced an improvement in the proportion of product. After addition of another 0.38 ml of ethyl chloroformate and 3 more hours of reflux, the mixture was cooled to room temperature, poured into a separatory funnel, and washed with water ($2 \times 100$ ml) to remove unreacted starting material as the hydrochloride salt. The chloroform phase was washed with 200 ml of saturated sodium chloride solution and thereafter dried over anhydrous sodium sulfate. Filtration of the mixture and concentration of the filtrate in vacuo afforded 4.7 g of a gum which TLC showed to be a product essentially free of unreacted starting material. This material was dissolved in 150 ml of ether, gravity-filtered to remove insoluble material, and the filtrate was concentrated in vacuo to a gum weighing 4.07 g. This material was taken up in 50 ml of ether and filtered, and hydrogen chloride-saturated ether was added to the filtrate. Crude hydrochloride formed as a gum which was solidified by decanting the liquid, rinsing twice with fresh ether and triturating with a third portion of fresh ether. Filtration and drying in vacuo afforded 3.62 g of solid. Recrystallization twice from absolute ethanol/ether afforded 2.25 g of solid, m.p. 201°-204° dec.

ANALYSIS: Calculated for $C_{23}H_{29}N_3O_2.HCl$: 66.41%C; 7.27%H; 1 10.10%N; Found: 66.67%C; 7.41%H; 9.79%N;

EXAMPLE 5

N,N-Dimethyl-7-(methylamino)carbonyl-1,2,6,7-tetrahydrobenzo[b]pyrrolo[3,2,1-jk][1,4]benzodiazepine-6-propanamine hydrochloride To a solution of 6.26 g of N,N-dimethyl-1,2,6,7-tetrahydrobenzo[b]pyrrolo[3,2,1-jk][1,4]benzodiazepine-6-propanamine in 125 ml of dry toluene was added 2.36 ml of methyl isocyanate, via syringe, under nitrogen. After stirring the mixture overnight at room temperature it was diluted with ether (500 ml) and the resulting solution was washed with water ($2 \times 250$ ml) and saturated sodium chloride solution and thereafter dried over anhydrous sodium sulfate. Filtration and concentration in vacuo afforded a foam weighing 6.72 g. This material was dissolved in 5:1 ether/methanol solution (approx. 150 ml) and treated dropwise with hydrogen chloride-saturated ether solution with stirring. Crude salt formed as an insoluble oil on the side wall of the flask. After a few minutes of stirring, the liquid phase was decanted and fresh ether used to triturate the crude salt to a solid.

Filtration and drying in vacuo afforded 6.72 g of solid. This material was combined with some crude salt prepared in an analogous manner and dissolved in 25 ml of boiling isopropanol. The hot solution was gravity-filtered, allowed to cool and stand at room temperature for a few minutes and then was refrigerated overnight. The recrystallized salt was filtered, washed twice with cold isopropanol, and ether and dried in vacuo to afford 4.7 g of crystalline solid, m.p. 233°–235° C.

ANALYSIS: Calculated for $C_{22}H_{28}N_4O \cdot HCl$: 65.90%C; 7.29%H; 13.98%N; Found: 65.62%C; 7.49%H; 13.49%N;

EXAMPLE 6

N,N-Dimethyl-7-(phenylamino)carbonyl-1,2,6,7-tetrahydrobenzo[b]pyrrolo[3,2,1-jk][1,4]benzodiazepine-6-propanamine hydrochloride A mixture of 9.84 g of N,N-dimethyl-1,2,6,7-tetrahydro benzo[b]pyrrolo[3,2,1-jk][1,4]benzodiazepine-6-propanamine, 200 ml of toluene and 7.0 ml of phenyl isocyanate was stirred overnight at room temperature under nitrogen. Concentration of the reaction mixture in vacuo yielded a gum which solidified upon standing This material was triturated with petrdleum ether, filtered and dried to afford 13.65 g of a solid. This crude free base was dissolved in 75 ml of warm methanol and the resulting solution was gravity-filtered. The filtrate was degassed with nitrogen and made acidic with hydrogen chloride-saturated ether solution, and then degassed again with nitrogen. To this solution 150 ml of ether was added dropwise with stirring. The light brown liquid phase was decanted, and the gummy, dark blue precipitate was triturated fully to a solid with fresh ether. Filtration and drying afforded 9.33 g of crude hydrochloride salt as a solid. Recrystallization of this material from 200 ml of absolute ethanol afforded 4.35 g of fine crystals, m.p. 247°–249° C. with bubbling.

ANALYSIS: Calculated for $C_{27}H_{30}N_4O \cdot HCl$: 70.04%C; 6.75%H; 12.10%N; Found: 69.77%C; 6.86%H; 11.96%N;

EXAMPLE 7

4-Bromo-N,N-dimethyl-1,2,6,7-tetrahydrobenzo[b]pyrrolo[3,2,1-jk]1,4]benzodiazepine-6-propanamine dihydrochloride In a dried 1 liter 3-necked flask, 1,2-dibromoethane was added to a refluxing slurry of magnesium (8 g) chips in tetrahydrofuran (30 ml) to initiate a Grignard reaction. The mixture became cloudy and a vigorous reaction ensued. A solution of 3-(dimethylamino)propyl chloride (32 g) in tetrahydrofuran (100 ml) was added dropwise to maintain fast refluxing over a period of 20 minutes. The final mixture was refluxed for 1 hour and cooled to room temperature.

The freshly prepared Grignard reagent was decanted into a dropping funnel, and added dropwise to a rapidly stirred solution of 4-bromo-1,2-dihydrobenzo[b]pyrrolo[3,2,1-jk][1,4]benzodiazepine (26 g) in tetrahydrofuran (200 ml) at 0° C. The final solution was stirred at room temperature for 2 hours.

The product solution was poured into a mixture of ice and concentrated hydrochloric acid (1 liter/100 ml), stirred for 10 minutes and basified with ammonium hydroxide to pH=9. Some precipitate formed, which was collected by filtation. The aqueous solution was extracted with dichloromethane (2×500 ml). The organic solution was washed with water (700 ml) and brine (3×700 ml), dried over anhydrous sodium sulfate and concentrated to afford a solid (19 g). Recrystallization from hot isopropanol (500 ml) gave 14.5 g of crystals, m.p. 162°–164° C.

The mother liquor was concentrated and the solid from the filtrate (about 7.5 g) was treated with 3 equivalents of hydrochloric acid in methanol and concentrated down to a solid. Recrystallization from hot methanol/ether afforded 7 g of pure dihydrochloride salt, m.p. 220° C., dec.

ANALYSIS: Calculated for $C_{20}H_{24}BrN_3 \cdot 2HCl$: 52.31%C; 5.71%H; 9.15%N; Found 51.97%C; 5.84%H; 9.00%N;

EXAMPLE 8

N-[3-[7-Acetyl-1,2,6,7-tetrahydrobenzo[b]pyrrolo[3,2,1-jk][1,4]-benzodiazepine-6-yl]propyl]-N-methylcarbamic Acid ethyl Ester A stirred suspension of 27.64 g of powdered anhydrous sodium bicarbonate in 415 ml of benzene containing 23.0 g of 7-acetyl-N,N-dimethyl-1,2,6,7-tetrahydrobenzo[b]pyrrolo[3,2,1-jk][1,4]benzodiazepine-6-propanamine was treated with 19.0 ml of ethyl chloroformate. After an overnight reflux under nitrogen, 6.3 ml more of ethyl chloroformate was added, and reflux continued another 2 hours. TLC still showed the presence of the starting material at this point, and a further addition of 6.3 ml of ethyl chloroformate was made. After 2 hours another 12.6 ml of ethyl chloroformate was added, reflux continued for another 1.5 hours, and the mixture cooled to room temperature. The reaction mixture was diluted with 500 ml of distilled water, stirred for a while, and poured into a separatory funnel, and the phases were separated. The aqueous phase was extracted with 250 ml of ethyl acetate. The combined organic phases were extracted with 200 ml of 2N hydrochloric acid, washed with 200 ml of water and 200 ml of saturated sodium chloride solution, and dried over anhydrous sodium sulfate. Filtration and concentration in vacuo afforded a gum weighing 24.37 g. This material was dissolved in 150 ml of dichloromethane, the resulting solution was divided into two halves, and each half was purified by flash chromatography on 500 g of silica gel, using dichloromethane and then 1% methanol/dichloromethane as solvent. The purest fractions were combined and concentrated in vacuo to a foam which partially crystallized upon standing. Trituration with hexane fully solidified this material, which was filtered, washed with hexane and dried in vacuo to afford 11.65 g of solid, m.p. 125°–128° C.

ANALYSIS: Calculated for $C_{24}H_{29}N_3O_3$: 70.74%C; 7.17%H; 10.31%N; Found: 70.88%C; 7.17%H; 10.32%N;

EXAMPLE 9

7-Acetyl-N-methyl-1,2,6,7-tetrahydrobenzo[b]pyrrolo[3,2,1-jk][1,4]benzodiazepine-6-propanamine hydrochloride A mixture of 11.45 g of N-[3-[7-acetyl-1,2,6,7-tetrahydrobenzo[b]pyrrolo[3,2,1-jk][1,4]benzodiazepine-6-yl]propyl]-N-methylcarbamic acid ethyl ester, 210 ml of absolute ethanol and 210 ml of 25% sodium hydroxide aqueous solution was refluxed for 72.5 hours under nitrogen, allowed to cool to room temperature and partitioned between 1.0 liter of distilled water and 500 ml of ethyl acetate. The phases were separated and the aqueous phase was extracted with another 250 ml of ethyl acetate. The combined organic extracts were washed with 100 ml of water and 100 ml of saturated sodium chloride solution and dried over anhydrous sodium sulfate. Filtration and concentration of the filtrate in vacuo afforded a crude solid, which was triturated with 2:1 petroleum ether/ether solution, filtered and dried to afford 7.05 g of solid. This material was dissolved in 50 ml of methanol, the solution was gravity-filtered, and the filtrate stirred and made acidic by the dropwise addition of 10 ml of hydrogen chloride-saturated ether solution. This acidic mixture was immediately degassed by bubbling nitrogen therethrough, and the solution was concentrated in vacuo to near dryness. The residue was stirred for a while in a stoppered flask with 125 ml of ether. The crude hydrochloride salt was filtered off, washed with ether and dried to afford 7.43 g of solid. Recrystallization from 475 ml of boiling isopropanol afforded 5.8 g of solid. m.p. 248°–251° with bubbling.

ANALYSIS: Calculated for $C_{21}H_{25}N_3O \cdot HCl$: 67.82%C; 7.05%H; 11.30%N; Found: 67.60%C; 7.19%H; 11.13%N;

EXAMPLE 10

N-Methyl-N-phenylmethyl-1,2,6,7-tetrahydrobenzo[b]pyrrolo[3,2,1-jk][1,4]benzodiazepine-6-propanamine hemi-fumarate To a suspension of 10.8 g of magnesium turnings in 50 ml of dry tetrahydrofuran was added approximately 1 ml of 1,2-dibromoethane, and the mixture was heated to initiate the reaction. A solution of 30.78 g of N-benzyl-N-methyl-3-chloropropylamine in 125 ml of tetrahydrofuran was added at a rapid drip, and after completion of the addition the mixture was refluxed under nitrogen for 1 hour. The mixture was cooled in ice water and a solution of 15.84 g of 1,2-dihydrobenzo[b]pyrrolo[3,2,1-jk][1,4]benzodiazepine in 100 ml of tetrahydrofuran was added over a 55 minute period, keeping the pot temperature less than or equal to 10° C. by controlling the rate of addition. After 30 minutes the mixture was decanted onto 1.25 liters of crushed ice containing 105 ml of concentrated hydrochloric acid and the mixture was stirred for a while. The mixture was then made basic by addition of 100 ml of concentrated ammonium hydroxide solution and extracted with ethyl acetate (1×500 ml, 1×250 ml). The combined ethyl acetate extracts were washed with 250 ml of distilled water and 250 ml of saturated sodium chloride solution and dried over anhydrous sodium sulfate. Filtration and concentration in vacuo afforded 40.1 g of an oil contaminated with N-benzyl-N-methylpropylamine. This liquid contaminant was removed by two flash chromatographies on silica gel (1190 g total), using hexane, 1:1 hexane/ethyl acetate, and finally ethyl acetate as solvent, as well as by trituration of the crude free base with hexane followed by filtration. These combined procedures afforded 14.89 g of free base, the purest portion of which had m.p. 84°–87° C. A 11.0 g portion of this material was dissolved in 60 ml of absolute ethanol and gravity-filtered, and the filtrate was treated with a solution of 3.66 g of fumaric acid in 140 ml of absolute ethanol, seeded with seeds of the hemi-fumarate previously prepared on a small scale and stirred overnight in a stoppered flask. Filtration of the salt, trituration and successive washing with ethanol and ether, and drying afforded 10.07 g of solid, m.p. 140.5°–145.5° C. Recrystallization of this material from 185 ml of boiling absolute ethanol, filtration of the boiling mixture, and stirring of the filtrate in a stoppered flask as it cooled to room temperature caused crystallization of the purified salt. After stirring for 1 hour at room temperature, the mixture was cooled in ice water with stirring for 3 hours. The recrystallized salt was then filtered off, triturated and washed with ethanol and ether, and dried to afford 8.83 g of solid, m.p. 142°–145° C.

ANALYSIS: Calculated for $C_{26}H_{29}N_3 \cdot 0.5\ C_4H_4O_4$: 76.15: %C; 7.08%H; 9.52%N; Found: 75.76%C; 7.22%H; 9.35%N;

EXAMPLE 11

4-Bromobenzo[b]pyrrolo[3,2,1-jk][1,4]benzodiazepine

A solution of 2,3-dichloro-5,6-dicyano-1,4-benzoquinone (DDQ, 22 g) in toluene (200 ml) was added dropwise to a refluxing solution of 4-bromo-1,2-dihydrobenzo[b]pyrrolo[3,2,1-jk][1,4]benzodiazepine (10 g) in toluene (750 ml) under nitrogen. The mixture was refluxed for 1 hour, cooled, stirred with triethylamine (3 g) for 10 minutes, and fed to a flash chromatography column (slurry packed with silica, 300 g in dichloromethane). The column was eluted with dichloromethane (4 liter); 1% methanol/dichloromethane (2 liter); 1% methanol/0.5% ammonium hydroxide/dichloromethane (2 liter), until the desired product was separated from the remaining quinone. The crude product (10 g) was purified carefully on a second flash chromatography column (silica gel, 180 g; eluted with 20:80% hexane/dichloromethane, 6 liter). The desired product was isolated as a solid (5.4 g). Recrystallization from ethanol (70 ml) gave crystals which turned to powder after vacuum drying at 110° C. The yield was 3.2 g, m.p. 122°–123° C.

ANALYSIS: Calculated for $C_{15}H_9BrN_2$: 60.63%C; 3.05%H; 9.34%N; Found: 60.58%C; 2.99%H; 9.38%N;

EXAMPLE 12

4-Bromo-N,N-dimethyl-6,7-dihydrobenzo[b]pyrrolo[3,2,1-jk][1,4]-benzodiazepine-6-propanamine fumarate hemihydrate In a 500 ml 3-necked flask, 1,2-dibromoethane (0.3 ml) was added to a refluxing slurry of magnesium (2 g) chips in tetrahydrofuran (40 ml) to initiate a reaction. A solution of 3-(dimethylamino)propylchloride (11 ml) in 50 ml of tetrahydrofuran was added rapidly. The mixture was refluxed for 50 minutes and cooled to 5° C.

4-Bromobenzo[b]pyrrolo[3,2,1-jk][1,4]benzodiazepine (5.8 g) in tetrahydrofuran (50 ml) was added slowly. After stirring for an additional 30 minutes, the solution was poured into ice water/concentrated hydrochloric acid (600 ml:20 ml) and the mixture was stirred for 20 minutes. The acidic solution was added to a mixture of dichloromethane (600 ml) and ammonium hydroxide (25 ml) with stirring. The dichloromethane solution was separated. The aqueous solution was extracted once more with dichloromethane (200 ml). The combined dichloromethane solutions were washed with water (400 ml) and brine (2×350 ml), dried over anhydrous magnesium sulfate and concentrated to a crude foam (7 g).

The foam was purified by flash chromatography over silica (115 g, packed with 1 liter dichloromethane and 5 ml of ammonium hydroxide, eluted with dichloromethane (2 liter) and 1.5% methanol/dichloromethane (2 liter)). Fractions containing pure desired product were pooled and concentrated to a.foam (3.4 g). Less pure fractions (1 g) were combined with a previously collected material (7.45 g) and re-chromatographed, whereupon an additional 6.4 g of pure product was obtained.

The fumarate salt was prepared by treating the free base with 1.05 equivalents of fumaric acid in ethanol with stirring The resultant crystals (about 12 g) were recrystallized from ethanol (300 ml) to yield 5.92 g of crystals, m.p. 130°–130.5° C.

ANALYSIS: Calculated for $C_{20}H_{22}BrN_3 \cdot C_4H_4O_4 \cdot 0.5H_2O$: 56.69%C; 5.34%H; 8.24%N; Found: 56.48%C; 5.38%H; 8.27%N;

EXAMPLE 13

9-Bromo-N,N-dimethyl-1,2,6,7-tetrahydrobenzo[b]pyrrolo[3,2,1-jk][1,4]benzodiazepine-6-propanamine dihydrochloride In a dried 1 liter 3-necked flask, 1,2-dibromoethane (0.3 ml) was added to a refluxing slurry of magnesium (6.49 g) chips in tetrahydrofuran (50 ml) to initiate a reaction. A solution of 3-(dimethylamino)propyl chloride (32 g) in tetrahydrofuran (50 ml) was added rapidly. The reaction mixture was refluxed for 1 hour and cooled to room temperature. A solution of 9-bromo-1,2-dihydrobenzo[b]pyrrolo[3,2,1-jk][1,4]benzodiazepine (16 g) in tetrahydrofuran (120 ml) was added in portions at room temperature and the mixture was stirred for 0.5 hour. The liquid portion was decanted into ice-hydrochloric acid (0.6 liter of ice/water plus 50 ml of concentrated hydrochloric acid). After 15 minutes, the mixture was transferred to a beaker containing dichloromethane (960 ml) and ammonium hydroxide (50 ml). After vigorous stirring, the organic phase was separated The basic aqueous phase was extracted once more with dichloromethane (300 ml). The combined organic solution was washed with brine (2×500 ml), dried over anhydrous magnesium sulfate and concentrated to a crude gum (21 g). This material was purified by flash chromatography on a silica gel column (silica:330 g; eluted with 6 liters of 4% methanol/dichloromethane and 2 liters of 5% methanol/dichloromethane). The desired product weighed 12.7 g.

The dihydrochloride salt was prepared by adding a solution of the free base (11.7 g) in ethanol to a solution consisting of ether (30 ml), ethanol (50 ml) and hydrogen chloride (the hydrogen chloride was generated in situ from 7.0 g of acetyl chloride at 0° C. Recrystallization from hot ethanol (1.2 liter) gave 5.6 g of pure crystals, m.p. 228°–231° C., dec.

ANALYSIS: Calculated for $C_{20}H_{24}BrN_3 \cdot 2HCl$: 52.31%C; 5.71%H; 9.15%N; Found: 52.22%C; 5.95%H; 9.08%N;

EXAMPLE 14

4-Bromo-N,N-dimethyl-7-formyl-1,2,6,7-tetrahydrobenzo[b]pyrrolo[3,2,1-jk][1,4]benzodiazepine-6-propanamine Acetic anhydride (7.8 ml) and formic acid (12.5 ml) were mixed together and stirred at −10° C. for 1 hour. This solution now containing formic-acetic mixed anhydride was added to a solution of 4-bromo-N,N-dimethyl-1,2,6,7-tetrahydrobenzo[b]pyrrolo[3,2,1-jk][1,4]benzodiazepine-6-propanamine (21.3 g) in chloroform (250 ml) at room temperature in one portion. The resulting solution was shaken for 30 minutes The reagent and solvent were removed on a rotary evaporator to give a foam-oil mixture. This was dissolved into dichloromethane and water and the mixture was basified with 10% sodium hydroxide. The organic phase was separated, washed with water and brine (2×250 ml) and dried over anhydrous magnesium sulfate. Removal of the solvent gave an oily crude product. Purification was conducted by flash chromatography on silica gel (140 g) eluted with 2 liters of dichloromethane, 2 liters of 1% methanol/dichloromethane and 2 liters of 2% methanol/dichloromethane. Fractions containing the pure product were combined and concentrated to afford 14.7 g of solid. Recrystallization from ethanol (40 ml) at 0° C. gave 10.6 g of crystals, m.p. 126°–127° C.

ANALYSIS: Calculated for $C_{21}H_{24}BrN_3O$: 60.87%C; 5.84%H; 10.14%N; Found: 60.81%C; 6.13%H; 10.04%N;

EXAMPLE 15

6-Cyano-1,2,6,7-tetrahydrobenzo[b]pyrrolo[3,2,1-jk][1,4]-benzodiazepine

Acetic acid (30 ml) was added to a slurry consisting of sodium cyanide (10 g), 1,2-dihydrobenzo[b]pyrrolo[3,2,1-jk][1,4]-benzodiazepine (19 g) and ethyl acetate (250 ml) dropwise at room temperature. The mixture was stirred for 18 hours and thereafter diluted with ethyl acetate to 1 liter and washed with 1N sodium hydroxide (2×500 ml), water (2×600 ml) and brine (2×600 ml) The solution was dried over anhydrous magnesium sulfate and concentrated to a solid. The solid was triturated with ether (2×150 ml). Recrystallization from hot toluene (450 ml) yielded 14.8 g of crystals, m.p. 185°–186.5° C.

ANALYSIS: Calculated for $C_{16}H_{13}N_3$: 77.71%C; 5.30%H; 17.00%N; Found: 77.67%C; 5.28%H; 16.98%N;

EXAMPLE 16

1,2,6,7-Tetrahydrobenzo[b]pyrrolo[3,2,1-jk][1,4]benzodiazepine6-methanamine

6-Cyano-1,2,6,7-tetrahydrobenzo[b]pyrrolo[3,2,1-jk][1,4]benzodiazepine (15 g) was added to 300 ml of a 1M solution of diisobutylaluminium hydride in dichloromethane at −78° C. The reaction mixture was stirred for 3 hours at low temperature and thereafter diluted to 1 liter with dichloromethane. The excess hydride was slowly decomposed with methanol (50 ml). The gelatinous solution was washed with 5% sodium hydroxide (500 ml) and brine (2×500 ml) and dried over anhydrous sodium sulfate. The solution was filtered and concentrated to a solid-oil mixture (15.2 g). Purification was effected by flash chromatography over silica gel (145 g, eluted with 3.5% methanol/dichloromethane) to afford 7.7 g of product. Recrystallization from hot ethanol (65 ml) yielded 6.2 g of crystals, m.p. 171.5°–172.5° C.

ANALYSIS: Calculated for $C_{16}H_{17}N_3$: 76.46%C; 6.82%H; 16.72%N; Found 76.24%C ; 6.80%H; 16.55%N;

EXAMPLE 17

N-(Methylethylidene)-1,2,6,7-tetrahydrobenzo[b]pyrrolo[3,2,1-jk][1,4]benzodiazepine-6-methanamine 6-Cyano-1,2,6,7-tetrahydrobenzo[b]pyrrolo[3,2,1-jk][1,4]benzodiazepine (1.0 g) was added to 20 ml of a 1M solution of diisobutylaluminium hydride in dichloromethane at −78° C. (dry ice-acetone) in one portion. The mixture was stirred at low temperature for 1 hour and thereafter diluted to 150 ml with dichloromethane, and the excess hydride was slowly destroyed with methanol. The gelatinous solution was washed with 1N sodium hydroxide (200 ml) and brine (300 ml), dried over anhydrous sodium sulfate and filtered. The solution was concentrated to an oil (about 1 g). This crude product was purified by flash chromatography (9 g, silica; eluted with 5% methanol/dichloromethane, 200 ml). The resultant material (500 mg) was recrystallized from acetone (7 ml), whereupon it reacted with acetone and formed 410 mg of the above-identified Schiff base, m.p. 115°–116° C.

ANALYSIS: Calculated for $C_{19}H_{21}N_3$: 78.32%C; 7.26%H; 14.42%N; Found: 78.04%C; 7.32%H; 14.50%N;

EXAMPLE 18

N-(Isopropyl)-1,2,6,7-tetrahydrobenzo[b]pyrrolo[3,2,1-jk][1,4]-benzodiazepine-6-methanamine dihydrochloride hemihydrate Sodium cyanoborohydride ($NaBH_3CN$, 5 g) was added to a solution of N-(methylethylidene)-1,2,6,7-tetrahydrobenzo[b]-pyrrolo[ 3,2,1-jk][1,4]benzodiazepine-6-methanamine (9.0 g) in acetonitrile (250 ml) at 5° C. over a 1 hour period. Additional sodium cyanoborohydride (4.9 g) was added and the mixture was stirred for 2 hours. At the end of the reaction, the excess reagent was destroyed with methanol. The solvent was removed with a rotary evaporator. The residue was partitioned between dichloromethane (1 liter) and water (600 ml). The dichloromethane solution was separated and washed with brine (3×600 ml), dried over anhydrous sodium sulfate and concentrated to a crude oil.

Purification was conducted by flash chromatography over silica (140 g, eluted with 2% methanol/dichloromethane). Fractions containing pure product were pooled and concentrated to an oil. Treatment of this oil with methanol/hydrogen chloride and ether, gave 6.19 g of crystals, m.p. 218°–220° C.

ANALYSIS: Calculated for $C_{19}H_{23}N_2.2HCl.0.5 H_2O$: 60.80%C; 6.98%H; 11.20%N; Found 61.25%C; 7.06%H; 11.47%N;

EXAMPLE 19

N-[[7-Formyl-1,2,6,7-tetrahydrobenzo[b]pyrrolo[3,2,1-jk][1,4]-benzodiazepine-6-yl]methyl]-formamide Acetic anhydride (8.0 ml) and formic acid (9.12 ml) were mixed together and stirred at −10° C. (methanol-/ice) for 1 hour. This solution now containing formic-acetic acid mixed anhydride was added to a solution of 1,2,6,7-tetrahydrobenzo[b]pyrrolo[3,2,1-jk][1,4]benzodiazepine-6-methanamine (10.0 g) in chloroform (250 ml) at 0° C. in one portion. The mixture was handshaken for 20 minutes. The final solution was treated with excess methanol and concentrated to an oil. Purification was conducted by flash chromatography on silica gel (170 g, eluted with 2 liters of dichloromethane and 2 liters of 2% methanol/dichloromethane). Fractions containing the pure product were pooled and concentrated to a solid, (11.17 g). Recrystallization from hot ethanol (370 ml) gave 9.51 g of crystals, m.p. 201°–202° C.

ANALYSIS: Calculated for $C_{18}H_{17}N_3O_2$: 70.34%C; 5.58%H; 13.67%N; Found: 70.34%C; 5.72%H; 13.64%N;

EXAMPLE 20

N-Methyl-7-methyl-1,2,6,7-tetrahydrobenzo[b]pyrrolo[3,2,1-jk][1,4]benzodiazepine-6-methanamine dihydrochloride To a stirred solution of N-[7-formyl-1,2,6,7-tetrahydrobenzo[b]pyrrolo[3,2,1-jk][1,4]benzodiazepin-6-ylmethyl]-formamide (8.27 g) in tetrahydrofuran (220 ml) was added borane-dimethylsulfide complex in tetrahydrofuran (2M, 67 ml) at room temperature under nitrogen over a period of 30 minutes. The mixture was stirred at room temperature for 2 hours and thereafter refluxed for 30 minutes. The mixture was cooled to room temperature and treated slowly with methanol to destroy the excess borane. The solvent was removed with a rotary evaporator to afford an oil. This was dissolved in methanol (25 ml) and concentrated hydrochloric acid (8 ml), and the mixture was refluxed for 30 minutes. The mixture was concentrated on a rotary evaporator to dryness (55° C., high vacuum) to afford an oil. The oil was crystallized from a mixture of methanol (small amount) and ether (200 ml) to give 9.27 g of crystals. This solid was recrystallized from hot methanol (25 ml) to give 6.37 g of crystals, m.p. 194°–196.5° C.

ANALYSIS: Calculated for $C_{18}H_{21}N_3.2HCl$: 61.36%C; 6.58%H; 11.93%N; Found: 61.02%C; 6.89%H; 11.70%N;

EXAMPLE 21

N-[[1,2,6,7-Tetrahydrobenzo[b]pyrrolo[3,2,1-jk][1,4]benzodiazepine-6-yl]methyl]-formamide 1,2,6,7-Tetrahydrobenzo[b]pyrrolo[3,2,1-jk][1,4]benzo-diazepine-6-methanamine (10 g), ethanol (100 ml) and methylformate (150 ml) were combined in a 500 ml 3-neck flask fitted with a condenser and nitrogen inlet. The mixture was refluxed 16 hours. Methylformate and ethanol were removed under reduced pressure The residue was purified by flash column chromatography (silica, 200 g; eluted with 1% methanol/dichloromethane). The purest fractions were concentrated to afford 6.9 g of a solid. Recrystallization twice from hot methanol afforded 3.6 g of crystals, m.p. 169°–170° C.

ANALYSIS: Calculated for $C_{17}H_{17}N_3O$: 73.08%C; 6.15%H; 15.04%N; Found: 73.00%C; 6.15%H; 15.23%N;

EXAMPLE 22

N-Methyl-1,2,6,7-tetrahydrobenzo[b]pyrrolo[3,2,1-jk][1,4]-benzodiazepine-6-methanamine Lithium aluminium hydride (5.6 g) was charged to a solution of N-[1,2,6,7-tetrahydrobenzo[b]pyrrolo[3,2,1-jk][1,4]benzodiazepine-6-ylmethyl]-formamide (10.3 g) in tetrahydrofuran (300 ml) at 0° C. under nitrogen in two portions (two hours apart). The mixture was stirred at room temperature overnight. The excess lithium aluminum hydride was destroyed carefully with water (6 ml) and sodium hydroxide (6 ml) at 0° C. The mixture was stirred with an additional 18 ml of water for 1 hour. The aluminium salts were filtered off. The tetrahydrofuran solution was concentrated to a foam. This material was dissolved in dichloromethane (200 ml) and washed with brine (200 ml). The solvent was removed and the crude product purified by flash chromatography over a silica gel column (100 g of silica, eluted with 2% methanol/dichloromethane) to afford 9.8 g of product. Recrystallization from hot ethanol (50 ml) yielded 6.18 g of crystals, m.p. 126°-127° C.

ANALYSIS: Calculated for $C_{17}H_{19}N_3$: 76.95%C; 7.22%H; 15.84%N; Found: 77.09%C; 7.38%H; 15.75%N;

EXAMPLE 23

1,2,6,7-Tetrahydrobenzo[b]pyrrolo[3,2,1-jk][1,4]benzodiazepine6-acetonitrile n-Butyllithium (10 ml of a 2.5M solution) and tetrahydrofuran (THF, 10 ml) were placed in a 250 ml 3-neck flask under nitrogen and chilled to −60° C. (dry ice-/acetone). Acetonitrile (1 g) in tetrahydrofuran (10 ml) was added in one portion. A precipitate formed in a short time. Thirty minutes thereafter, a solution of 1,2-dihydrobenzo[b]pyrrolo[3,2,1-jk][1,4]benzodiazepine (4.5 g) in tetrahydrofuran (20 ml) was added. The cold bath was then removed and the reaction mixture was stirred for 2 hours. The mixture was diluted with ethyl acetate (350 ml) and poured into saturated ammonium chloride solution (500 ml). The organic phase was separated and washed with brine (50%, 500 ml). The insolubles were collected by filtration. The ethyl acetate solution was dried over anhydrous sodium sulfate and concentrated to a solid. The solids were combined and purified by flash chromatography (silica, 80 g, eluted with dichloromethane) to afford 4.2 g of product. Recrystallization from a large volume of ethanol/isopropanol gave 2.48 g of crystalline product, m.p. 218°-220° C.

ANALYSIS: Calculated for $C_{17}H_{15}N_3$: 78.14%C; 5.79%H; 16.08%N; Found: 78.22%C; 5.74%H; 16.03%N;

EXAMPLE 24

1,2,6,7-Tetrahydrobenzo[b]pyrrolo[3,2,1-jk][1,4]benzodiazepine-6-ethanamine fumarate Lithium aluminium hydride (6.8 g) was added to a stirred solution of 1,2,6,7-tetrahydrobenzo[b]pyrrolo[3,2,-jk][1,4]-benzodiazepine-6-acetonitrile (11.7 g) in tetrahydrofuran (300 ml) at 0° C. under nitrogen in small portions. The mixture was stirred at room temperature for 2.5 hours, when TLC indicated there was no more starting material left. The excess lithium aluminium hydride was carefully hydrolyzed with water (7 ml). To the mixture were added 10% sodium hydroxide (7 ml) and water (21 ml), and stirring was continued for 1 hour. The gelatinous solid was filtered off. The solution was concentrated almost to dryness on a rotary evaporator. The crude residue was dissolved in dichloromethane (350 ml), washed with water (2×200 ml) and brine (2×300 ml) and dried over anhydrous sodium sulfate. The solution was concentrated to a foam product (13 g). This material was treated with fumaric acid (5.2 g) in ethanol to give the fumarate salt of the product (14.7 g). A repetitive recrystallization was conducted from hot ethanol (filtering off each time a small amount of insoluble material), and the solid was cooled to room temperature and treated with ether to afford in two crops 3.2 g of crystalline powder, m.p. 202°-204° C.

ANALYSIS: Calculated for $C_{17}H_{19}N_3 \cdot C_4H_4O_4$: 66.13%C; 6.08%H; 11.02%N; Found 65.75%C; 6.16%H; 11.00%N;

EXAMPLE 25

N-[[1,2,6,7-tetrahydrobenzo[b]pyrrolo[3,2,1-jk][1,4]benzodiazepine-6-yl]ethyl]-acetamide Lithium aluminum hydride (8.8 g) was added to a solution of 1,2,6,7-tetrahydrobenzo[b]pyrrolo[3,2,1-jk][1,4]benzodiazepine-6-acetonitrile (15 g) in tetrahydrofuran (200 ml) in small portions at −10° C. (methanol/ice) under nitrogen. The suspension was stirred at ambient temperature for 3.5 hours. At the end, ethyl acetate was added slowly at 0° C. to destroy the excess hydride, and the mixture was diluted further with ethyl acetate to a volume of 800 ml and allowed to stand overnight. The solids were filtered. The ethyl acetate was removed at reduced pressure. The residue was dissolved into dichloromethane (850 ml) and the insolubles were filtered off. The dichloromethane solution was washed with water (2×1 liter) and brine (2×500 ml), dried over anhydrous magnesium sulfate and concentrated to a crude solid (16 g). Purification was effected by flash chromatography (silica, 185 g, eluted with 2 liters of 2.5% methanol/dichloromethane and 2 liters of 4% methanol/dichloromethane). The purified material (8 g) was recrystallized from ethanol (200 ml) to give 4.6 g of crystals, m.p. 196.5°-198° C.

ANALYSIS: Calculated for $C_{19}H_{21}N_3O$: 74.24%C; 6.89%H; 13.67%, Found 74.27%C;, 6.94%H; 13.50%N;

We claim:

1. A compound of the formula

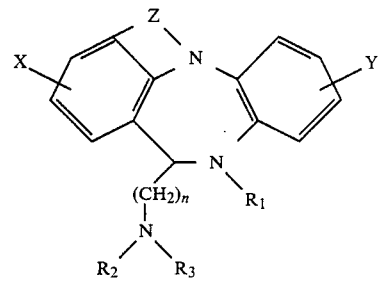

where X and Y are independently hydrogen, loweralkyl, trifluoromethyl or halogen; Z is —CH$_2$CH$_2$—, —CH=CH—, or —CH$_2$CH$_2$CH$_2$—; n is 1,2 or 3; R$_1$ is hydrogen, loweralkanoyl, aroyl, ethoxycarbonyl, phenoxycarbonyl, loweralkylaminocarbonyl, arylaminocarbonyl, loweralkyl or arylmethyl; R$_2$ hydrogen or loweralkyl; R$_3$ is hydrogen, loweralkyl, ethoxycarbonyl, loweralkanoyl, or arylloweralkyl, or R$_2$ and R$_3$ taken together is isopropylidene, the term aryl in each occurrence signifying a phenyl group having 0, 1 or 2 substituents each of which being independently loweralkyl, loweralkoxy, halogen or CF$_3$, the term aroyl signifying

the term arylaminocarbonyl signifying

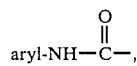

the term arylmethyl signifying aryl—CH$_2$— and the term arylloweralkyl signifying aryl-loweralkyl-; with the proviso that when n is 3, X, Y and R$_1$ are all hydrogen and Z is —CH$_2$CH$_2$—, R$_2$ and R$_3$ can not both be methyl; or a pharmaceutically acceptable acid addition salt thereof.

2. The compound as defined in claim 1, where Z is —CH$_2$CH$_2$—.

3. The compound as defined in claim 2, where in n is 3.

4. The compound as defined in claim 3, where X is hydrogen.

5. The compound as defined in claim 3, where X is halogen.

6. The compound as defined in claim 5, where x is bromine.

7. The compound as defined in claim 3, where Y is hydrogen.

8. The compound as defined in claim 3, where Y is halogen.

9. The compound as defined in claim 8, where Y is bromine.

10. The compound as defined in claim 3, where R$_1$ is formyl or methyl.

11. The compound as defined in claim 2, where n is 2.

12. The compound as defined in claim 11, where X is hydrogen.

13. The compound as defined in claim 11, where Y is hydrogen.

14. The compound as defined in claim 11, where X and Y are both hydrogen.

15. The compound as defined in claim 2, where n is 1.

16. The compound as defined in claim 15, where X is hydrogen.

17. The compound as defined in claim 15, where Y is hydrogen.

18. The compound as defined in claim 15, where X and Y are both hydrogen.

19. The compound as defined in claim 1, where Z is —CH=CH—.

20. The compound as defined in claim 19, where n is 3.

21. The compound as defined in claim 20, where X is hydrogen.

22. The compound as defined in claim 20, where X is halogen.

23. The compound as defined in claim 20, where X is bromine.

24. The compound as defined in claim 20, where Y is hydrogen.

25. The compound as defined in claim 20, where Y is halogen.

26. The compound as defined in claim 20, where Y is bromine.

27. The compound as defined in claim 1, which is 7-benzoyl-N,N-dimethyl-1,2,6,7-tetrahydrobenzo[b]pyrrolo[3,2,1-jk][1,4]-benzodiazepine-6-propanamine.

28. The compound as defined in claim 1, which is 7-acetyl-N,N-dimethyl-1,2,6,7-tetrahydrobenzo[b]pyrrolo[3,2,1-jk][1,4]-benzodiazepine-6-propanamine.

29. The compound as defined in claim 1, which is N,N-dimethyl-7-ethoxycarbonyl-1,2,6,7-tetrahydrobenzo[b]pyrrolo[3,2,1-jk][1,4]benzodiazepine-6-propanamine.

30. The compound as defined in claim 1, which is N,N-dimethyl-(methylamino)carbonyl-1,2,6,7-tetrahydrobenzo[b]pyrrolo[3,2,1-jk][1,4]benzodiazepine-6-propanamine.

31. The compound as defined in claim 1, which is N,N-dimethyl-7-(phenylamino)carbonyl-1,2,6,7-tetrahydrobenzo[b]pyrrolo[3,2,1-jk][1,4]benzodiazepine-6-propanamine.

32. The compound as defined in claim 1, which is 4-bromo-N,N-dimethyl-1,2,6,7-tetrahydrobenzo[b]pyrrolo[3,2,1-jk][1,4]-benzodiazepine-6-propanamine.

33. The compound as defined in claim 1, which is 4-bromo-7-methyl-N,N-dimethyl-1,2,6,7-tetrahydrobenzo[b]pyrrolo[3,2,1-jk]-benzodiazepin-6-propanamine.

34. The compound as defined in claim 1, which is N-[3-[7-acetyl-1,2,6,7-tetrahydrobenzo[b]pyrrolo[3,2,1-jk][1,4]-benzodiazpeine-6-yl]propyl]-N-methylcarbamic acid ethyl ester.

35. The compound as defined in claim 1, which is 7-acetyl-N-methyl-1,2,6,7-tetrahydrobenzo[b]pyrrolo[3,2,1-jk][1,4]-benzodiazepine-6-propanamine.

36. The compound as defined in claim 1, which is N-methyl-N-phenylmethyl-1,2,6,7-tetrahydrobenzo[b]pyrrolo[3,2,1-jk][1,4]-benzodiazepine-6-propanamine.

37. The compound as defined in claim 1, which is 4-bromo-N,N-dimethyl-6,7-dihydrobenzo[b]pyrrolo[3,2,1-jk][1,4]benzodiazepine-6-propanamine.

38. The compound as defined in claim 1, which is 9-bromo-N,N-dimethyl-1,2,6,7-tetrahydrobenzo[b]pyrrolo[3,2,1-jk][1,4]-benzodiazepine-6-propanamine.

39. The compound as defined in claim 1, which is N,N-dimethyl9-trifluoromethyl-1,2,6,7-tetrahydrobenzo[b]pyrrolo[3,2,1-jk]-[1,4]benzodiazepine-6-propanamine.

40. The compound as defined in claim 1, which is 4-bromo-N,N-dimethyl-7-formyl-1,2,6,7-tetrahydrobenzo[b]pyrrolo[3,2,1-jk][1,4]benzodiazepine-6-propanamine.

41. The compound as defined in claim 1, which is 1,2,6,7-tetrahydrobenzo[b]pyrrolo[3,2,1-jk][1,4]benzodiazepine-6-methanamine.

42. The compound as defined in claim 1, which is N-(methyl-ethylidene)-1,2,6,7-tetrahydrobenzo[b]pyrrolo[3,2,1-jk][1,4]-benzodiazepine-6-methanamine.

43. The compound as defined in claim 1, which is N-(isopropyl)1,2,6,7-tetrahydrobenzo[b]pyrrolo[3,2,1-jk][1,4]benzodiazepine-6-methanamine.

44. The compound as defined in claim 1, which is N-[[7-formyl-1,2,6,7-tetrahydrobenzo[b]pyrrolo[3,2,1-jk][1,4]-benzodiazepine-6-yl]methyl]-formamide.

45. The compound as defined in claim 1, which is N-methyl-7-methyl-1,2,6,7-tetrahydrobenzo[b]pyrrolo[3,2,1-jk][1,4]-benzodiazepine-6-methanamine dihydrochloride.

46. The compound as defined in claim 1, which is N-[[1,2,6,7-tetrahydrobenzo[b]pyrrolo[3,2,1-jk][1,4]benzodiazepine -6-yl]methyl]-formamide.

47. The compound as defined in claim 1, which is N-methyl1,2,6,7-tetrahydrobenzo[b]pyrrolo[3,2,1-jk][1,4]benzodiazepine6-methanamine.

48. The compound as defined in claim 1, which is 1,2,6,7-tetrahydrobenzo[b]pyrrolo[3,2,1-jk][1,4]benzodiazepine-6- ethanamine.

49. The compound as defined in claim 1, which is N-[[1,2,6,7-tetrahydrobenzo[b]pyrrolo[3,2,1-jk][1,4]benzodiazepine-6yl]ethyl]-acetamide.

50. A pharmaceutical composition which comprises an effective amount of a compound as defined in claim 1 and a carrier therefor.

51. A method of treating a patient in need of relief from inflammation which comprises administering to the patient an effective inflammation-alleviating amount of a compound as defined in claim 1.

52. A method of treating a patient in need of relief from pain which comprises administering to the patient an effective pain alleviating amount of a compound as defined in claim 1.

53. A method of treating a patient in need of relief from pain which comprises administering to the patient an effective pain alleviating amount of a compound as defined in claim 10.

54. A method of treating a patient in need of relief from pain which comprises administering to the patient an effective pain alleviating amount of a compound as defined in claim 40.

55. A method of treating a patient in need of relief from pain which comprises administering to the patient an effective pain alleviating amount of a compound as defined in claim 33.

56. A method of treating a patient in need of relief from inflammation which comprises administering to the patient an effective inflammation-alleviating amount of N,N-dimethyl 1,2,6,7-tetrahydrobenzo[b]pyrrolo[3,2,1-jk][1,4]benzodiazepine 6-propanamine.

57. A method of treating a patient in need of relief from pain which comprises administering to the patient an effective pain alleviating amount of N,N-dimethyl-1,2,6,7-tetrahydrobenzo[b]pyrrolo[3,2,1-jk][1,4]benzodiazepine-6-propanamine.

* * * * *